United States Patent
Schneider

(10) Patent No.: US 7,937,423 B2
(45) Date of Patent: *May 3, 2011

(54) SYSTEMS AND METHODS OF CONDUCTING CLINICAL RESEARCH

(75) Inventor: John K. Schneider, Snyder, NY (US)

(73) Assignee: Ultra-Scan Corporation, Amherst, NY (US)

(*) Notice: Subject to any disclaimer, the term of this patent is extended or adjusted under 35 U.S.C. 154(b) by 11 days.

This patent is subject to a terminal disclaimer.

(21) Appl. No.: 11/563,110

(22) Filed: Nov. 24, 2006

(65) Prior Publication Data

US 2007/0239782 A1 Oct. 11, 2007

Related U.S. Application Data

(60) Provisional application No. 60/739,607, filed on Nov. 23, 2005.

(51) Int. Cl.
*G06F 17/30* (2006.01)

(52) U.S. Cl. .......... 707/999.01; 707/966; 382/115; 382/116; 382/100; 340/286.02; 340/286.07

(58) Field of Classification Search ............... 707/102, 707/10, 966, 999.01; 706/15; 382/100, 115, 382/116; 340/286.01, 286.07

See application file for complete search history.

(56) References Cited

U.S. PATENT DOCUMENTS

| | | | | |
|---|---|---|---|---|
| 5,719,950 A * | 2/1998 | Osten et al. | ................... | 382/115 |
| 6,303,297 B1 * | 10/2001 | Lincoln et al. | ................... | 435/6 |
| 6,493,724 B1 * | 12/2002 | Cusack et al. | ............... | 707/104.1 |
| 7,054,823 B1 * | 5/2006 | Briegs et al. | ....................... | 705/2 |
| 7,082,415 B1 * | 7/2006 | Robinson et al. | ............... | 705/67 |
| 7,206,789 B2 * | 4/2007 | Hurmiz et al. | ................ | 707/102 |
| 7,440,929 B2 * | 10/2008 | Schneider et al. | .............. | 706/15 |
| 7,596,541 B2 * | 9/2009 | deVries et al. | ......................... | 1/1 |
| 2002/0060243 A1 * | 5/2002 | Janiak et al. | .................. | 235/382 |
| 2002/0089410 A1 * | 7/2002 | Janiak et al. | ................. | 340/5.53 |
| 2002/0097142 A1 * | 7/2002 | Janiak et al. | ................. | 340/5.53 |
| 2004/0006553 A1 * | 1/2004 | de Vries et al. | ................... | 707/1 |
| 2004/0122707 A1 * | 6/2004 | Sabol et al. | ....................... | 705/2 |
| 2004/0122708 A1 * | 6/2004 | Avinash et al. | ................... | 705/2 |
| 2006/0000296 A1 * | 1/2006 | Salter | ......................... | 73/863.01 |

* cited by examiner

*Primary Examiner* — Jean M Corrielus
(74) *Attorney, Agent, or Firm* — Hodgson Russ LLP

(57) ABSTRACT

Information management systems for clinical research, and related methods, are disclosed. The management system may have a database of biometric sample information. At least some of the pieces of sample information in the database may have been received from a test-subject in a first clinical research effort, and each piece of sample information may have a related pointer stored in the database. Each pointer may identify the location of clinical research information obtained during the first clinical research effort.

6 Claims, 5 Drawing Sheets

SYSTEMS AND METHODS OF CONDUCTING CLINICAL RESEARCH

CROSS-REFERENCE TO RELATED APPLICATION

This application claims the benefit of priority to U.S. provisional patent application Ser. No. 60/739,607, filed on Nov. 23, 2005.

FIELD OF THE INVENTION

The present invention relates to conducting clinical research.

BACKGROUND OF THE INVENTION

In collecting and maintaining medical research records it is a goal of the records management system to avoid duplicate records for a test-subject and at the same time insure that any given record is attributable to only a single test-subject. Furthermore, a clinical research facility in one location may utilize the services of a test-subject for a particular testing regimen, and then the test-subject may move to a different location and enroll in a different clinical research study at his or her new location. With each clinical research facility typically maintaining separate medical records for testing that the provider renders, the researchers may not have access to records about the people from previous testing. Such documents may include, for example, admission records, researcher notes, lab results and test results.

Each research establishment will normally identify a test-subject with a medical record number or account number of its own choosing in order to track medical records the facility generates in connection with the test-subject. In addition, each research establishment may keep the test-subject's records in a format or arrangement that is different from the format and arrangement used by another research establishment, thereby making it difficult for one research establishment to utilize the records of another research establishment.

In setting up the rules and procedures for managing the test-subjects of the clinical research facilities, and in order to make the research results more reliable, cost effective and deliver a higher reliability of information, it may be advantageous to collect all of a test-subject's medical and research records in a central location for access by other researchers and the peripheral organizations that service them. A central database of medical and research related information about its test-subjects enables a clinical research network to determine and set practices that help to reduce costs and improve the reliability of the results it ultimately provides to the pharmaceutical companies that are its customers. Duplicate record keeping is avoided and the accuracy of the contained data is less likely to be ambiguous. Ultimately the public is the beneficiary of this effort in that the pharmaceuticals are tested more thoroughly and reliably and result in better dosing, less unknown side effects and more confidence in the medications and results. However, managing such a database would be expensive, and would require many entities cooperating in a way that is currently not practical, and in some instances not desired by the entities collecting clinical research information.

What is needed is a means by which various clinical research facilities are able to access information about other clinical research test-subjects, without each clinical research facility being compliant with a predefined set of standards. This need can be served by the use of an electronic authorization system that is highly fraud-resistant, practical, convenient for the user, and yet cost-effective to deploy. More specifically, there is a need for an electronic authentication system that relies solely on an individual's physiological features (biometric) for event or transaction authorization, and does not require the individual to directly possess any personalized man-made memory devices or physical tokens such as smart cards, magnetic swipe cards, identification cards, driver's licenses or personal computers for identification.

SUMMARY OF THE INVENTION

The invention may use a database of biometric sample information wherein each piece of biometric sample information is related to at least one pointer. The pointer identifies the location of medical information in another database. Data that is stored somewhere in the network of databases may be located by providing a biometric of a test-subject. The biometric sample information and the related pointers may be stored in a central facility, which is available to authorized users of the system. In this manner, the various users of the system are not required to conform their own databases, and yet useful medical information is made available to those users. Security of the data may be established and maintained through the use of public/private key encryption and biometric authentication of any authorized users.

As such, a database of rules and standard entries may be maintained on a particular user's local computer system. Information about test-subjects and the related clinical research effort may also be stored on the local computer system. Another database may be linked to each of the local computer systems, and this central database may have pointers to the information that is stored on the local computer systems. In order to speed response time, the central database may store some of the medical information that is also stored on the local systems, and in those situations, the pointers may identify the medical information that is stored on the central database and/or the same information stored on the local computer system.

There may be many local computers linked to the central database. The various local systems might not have the same structure, type or programs. The local computers and the central database may each have the ability to query the other. Such a querying system (either locally or centrally) may have sufficient intelligence to determine that although a piece of information is not in the same format or position, that it is nevertheless decipherable and can be used, or portions of the information can be used, to satisfy a query for requested data. In this manner, a local computer may be provided with information from the centrally located database and/or another local computer, even though the structure, type and programs related to the information may be different. For example, a person's address or phone number might come from the local system, or if needed be acquired from a computer system in another geographic location. In order to assure that the information requested by a first location should be retrieved from a second location and then provided to the first location, the test-subject must have provided his biometric to each location. In order to reduce the size of the central database, all that is needed is for the central database to store the biometric and a related pointer to the second location—the information need not be stored in the central database.

The invention may be embodied as a clinical research management system. The management system may have a database of biometric sample information. At least some of the pieces of sample information in the database may have been received from a test-subject in a first clinical research effort, and each piece of sample information may have a related pointer stored in the database. Each pointer may identify the location of clinical research information obtained during the first clinical research effort.

The management system may also have a check-in facility at a clinical research facility that is conducting a second clinical research effort. The clinical research facility conducting the second clinical research effort may be the same clinical research facility that conducted the first clinical research effort, or it may be a different clinical research facility. The check-in facility may have a biometric reader suitable for obtaining a biometric specimen.

The management system may also have a microprocessor and a communication channel. The communication channel may link the microprocessor to the check-in facility. The microprocessor may be programmed to: (a) receive from the communication channel, information corresponding to a biometric specimen received at the check-in facility, (b) compare the biometric specimen to the biometric sample information (c) determine whether the specimen matches at least one piece of the sample information to identify a matching piece of sample information, (d) identify the pointer related to the matching piece of sample information, (e) use the pointer to obtain the corresponding clinical research information obtained during the first clinical research effort, and (f) provide the obtained corresponding clinical research information to the clinical research facility conducting the second clinical research effort.

The management system may further have a second database, the second database having stored therein the clinical research information obtained from the test-subject during the first clinical research effort.

The invention may be embodied as a network for managing clinical research. In such a network, there may be a first database of biometric sample information. At least some of the pieces of sample information may have been received from a test-subject participating in a first clinical research effort, and each of those pieces of sample information may have a related pointer to clinical research information obtained from the test-subject during the first clinical research effort. The network may have a plurality of check-in facilities, each check-in facility being located at a clinical research facility that is conducting clinical research that is not related to the first clinical research effort. Each of the check-in facilities may have a biometric reader.

Also in the network may be a microprocessor that is in communication with the check-in-facilities and the first database. The microprocessor may be programmed to: (a) receive a biometric specimen received at the biometric reader of one of the check-in facilities, (b) compare the biometric specimen to the biometric sample information (c) determine whether the specimen matches at least one piece of the sample information to identify a matching piece of sample information, (d) identify the pointer related to the matching piece of sample information, (e) use the identified pointer to obtain the corresponding clinical research information obtained during the first clinical research effort, (f) provide the obtained corresponding clinical research information to at least one of the clinical research facilities conducting clinical research that is not related to the first clinical research effort.

Furthermore, the network may include a plurality of second databases. Each of the second databases may have stored therein clinical research information pointed to by the pointers of the first database, and wherein at least one of the second databases has the clinical research information obtained during the first clinical research effort.

The invention may be embodied as method of managing clinical research. In one such method, a database may be provided. The database may have biometric sample information stored therein. Each piece of sample information may have been received from a test-subject in a first clinical research effort, and each piece of sample information may have a related pointer to clinical research information obtained during the first clinical research effort. The pointer may point to a database other than the database having the biometric specimen.

Further, in such a method, a prospective test-subject may be provided at a clinical research facility that is conducting a second clinical research effort, and a biometric specimen may be obtained from that prospective test-subject. The biometric specimen may be compared to the biometric sample information as part of an effort to determine whether the specimen matches any of the sample information. If the specimen matches at least one piece of sample information, then the related pointer may be used to obtain the corresponding clinical research information that was obtained during the first clinical research effort. The obtained clinical research information may be provided to the clinical research facility conducting the second clinical research effort and used to determine whether a problem is indicated with the prospective test-subject participating in the second clinical research effort. Once a determination is made as to whether a problem exists, action may be taken. For example, the prospective test-subject may be allowed to participate in the second clinical research effort if the determination does not indicate a problem. Or the prospective test-subject may be prevented from participating in the second clinical research effort if the determination indicates a problem.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

This invention may be embodied as a system, network or method which uses biometrics to authenticate an individual associated with a set of personal and/or demographic records so that the individual is positively identified before providing certain benefits as a result of the relationship with the individual. The demographic records may take the form of information related to, but not limited to, employment, healthcare, clinical research, or criminal activity. Further, the database system that hosts the records and biometric authentication system may be able to communicate and compare records with other similar database systems or those of a central authentication system and data repository system. Such a system may provide the user with information that exists in the database of another user of the system.

The invention may be used in situations where a test-subject enrolled in a clinical research study attempts to engage in a practice known as "study hoping". Study hoping occurs when a test-subject attempts to visit multiple clinical research facilities for the purpose of obtaining additional money. In other literature, the term "client" is used to refer to the "test-subject" identified in this application, and for ease of distinguishing features of the invention, we have elected to use the term "test-subject" herein. By using the invention, it may be possible to prevent or detect study hoping. For example, should the test-subject take a placebo under one study and actual trial pharmaceuticals under another at a different facility, then the results obtained for both studies might be invalidated. The same would also apply if a placebo was not used. In that case, the test-subject would be receiving multiple doses of a medication, or other medications, which may interfere with the results of the clinical research effort.

Another feature that may be afforded by the invention is verifying that the test-subject receiving the test medications is the one who is supposed to receive the medications, and not someone else. Verifying the identity of the test-subject may be performed either locally on the user's host system, or over a network or the internet with access to a plurality of records database systems. The invention also may be of particular importance in healthcare facilities where a test-subject is attempting to obtain drugs from several sources by visiting different doctors and clinics.

Figure 3:
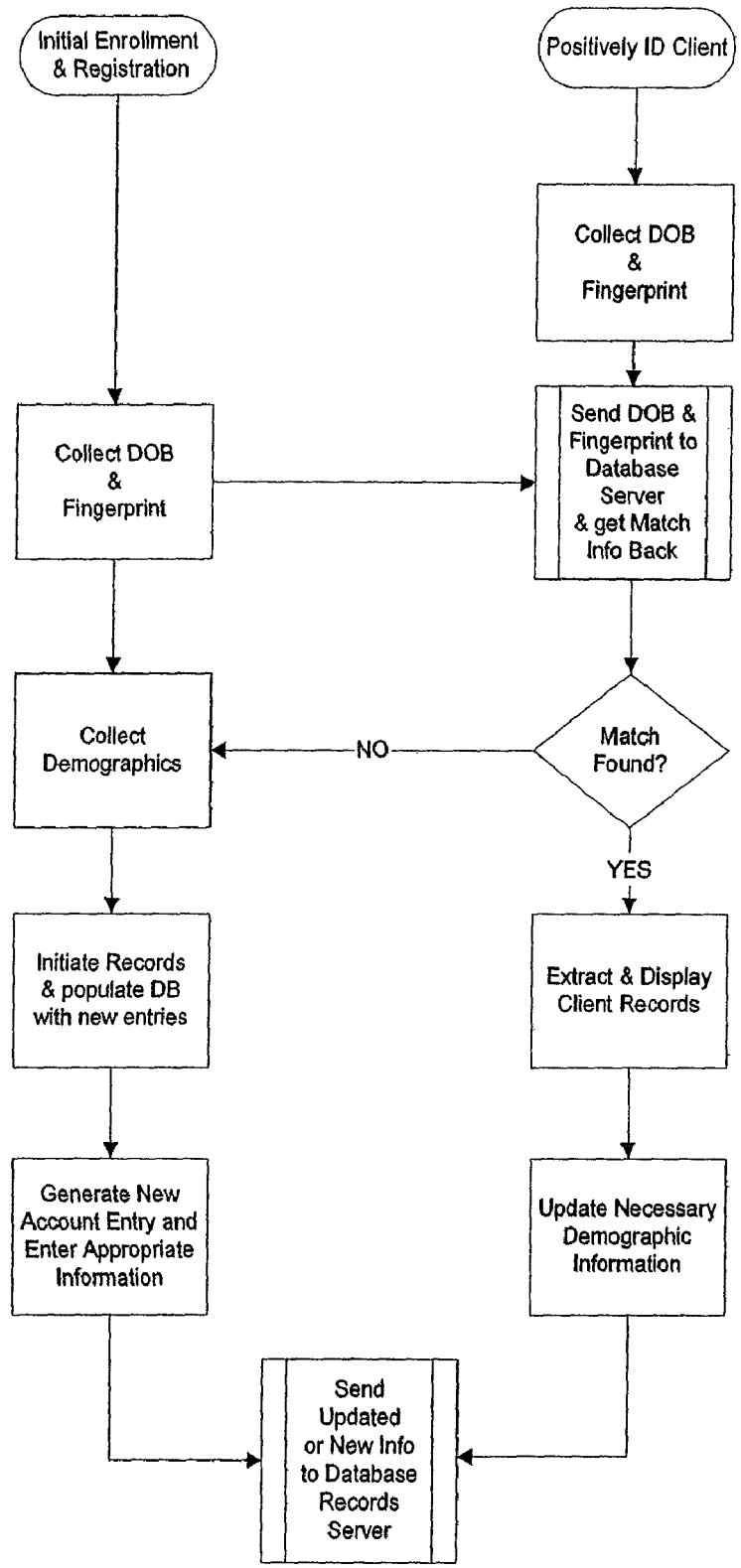
FIG. 3 is a flow diagram of an embodiment of the clinical research network client application according to the invention.

As a general overview of the invention, consider that a method according to the invention may use a biometric security system that verifies test-subject records pertaining to clinical research organizations or other health related information in a distributed database environment. The information databases may be maintained by different facilities and may safeguard information pertaining to the test-subjects and their respective medical records and histories. The biometric system may have a security shell network client application software program that works with an existing data management records system to intercept and control information that is of a private, confidential or secure nature. FIG. 3 outlines how such a security shell network client application software program might operate. The term "network client" will be used herein to refer to the client application in a client-server computer network. The security shell network client then communicates via communication channels of a network to gain access to information in other database systems by means of pointers that it acquires from a clinical research information data center. The database center may maintain a central data index of pointers to the locations of information in other databases. The database center may have an identity management database used to biometrically authenticate the identity of individuals using the system and accessing the information that it offers. The invention may establish biometric role-based event switching to accommodate individual transactions needing authorization that is of a transitory nature in its implementation.

Figure 1:
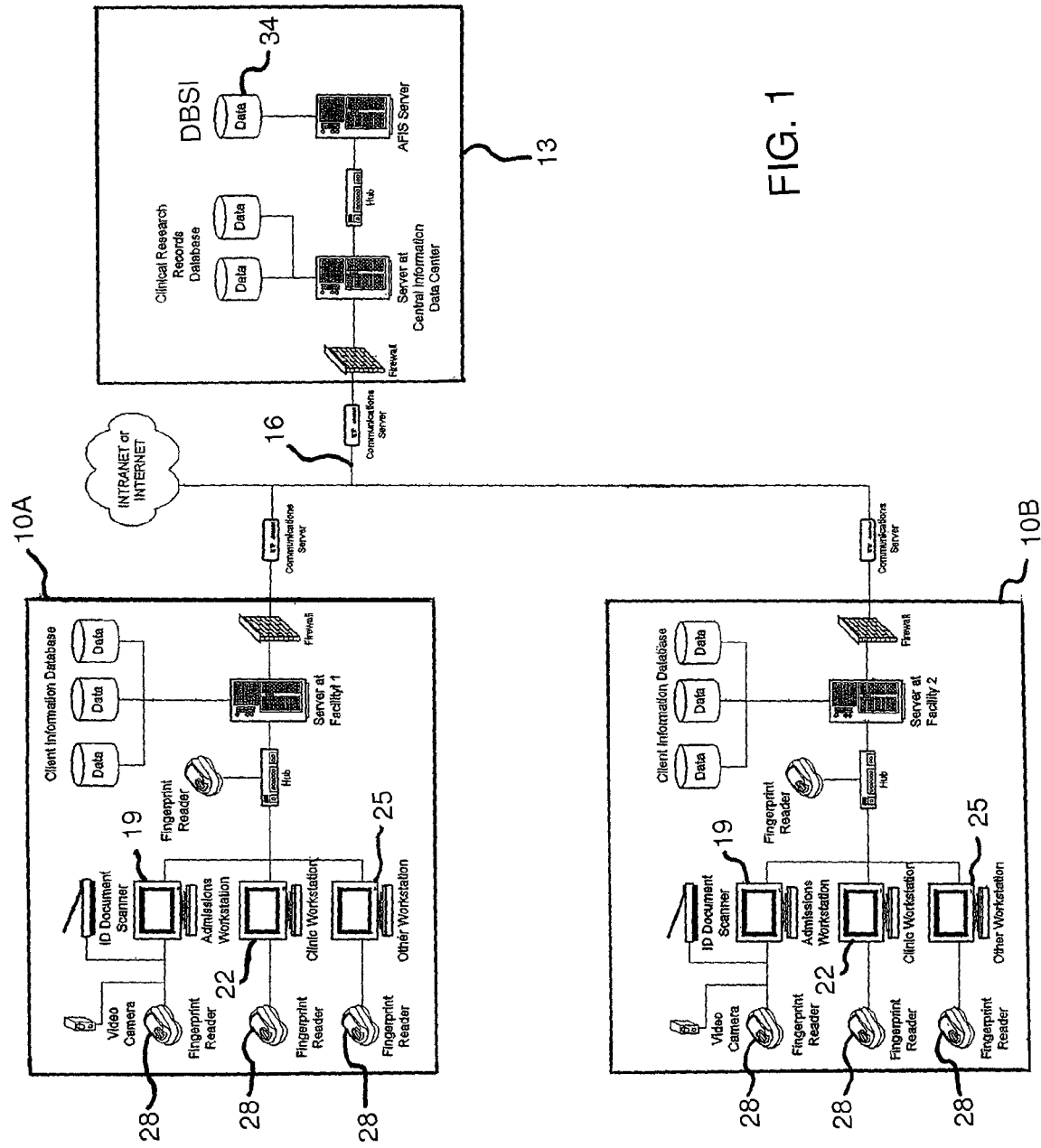
FIG. 1 is a schematic diagram representing a computer network according to the invention.
Figure 2:
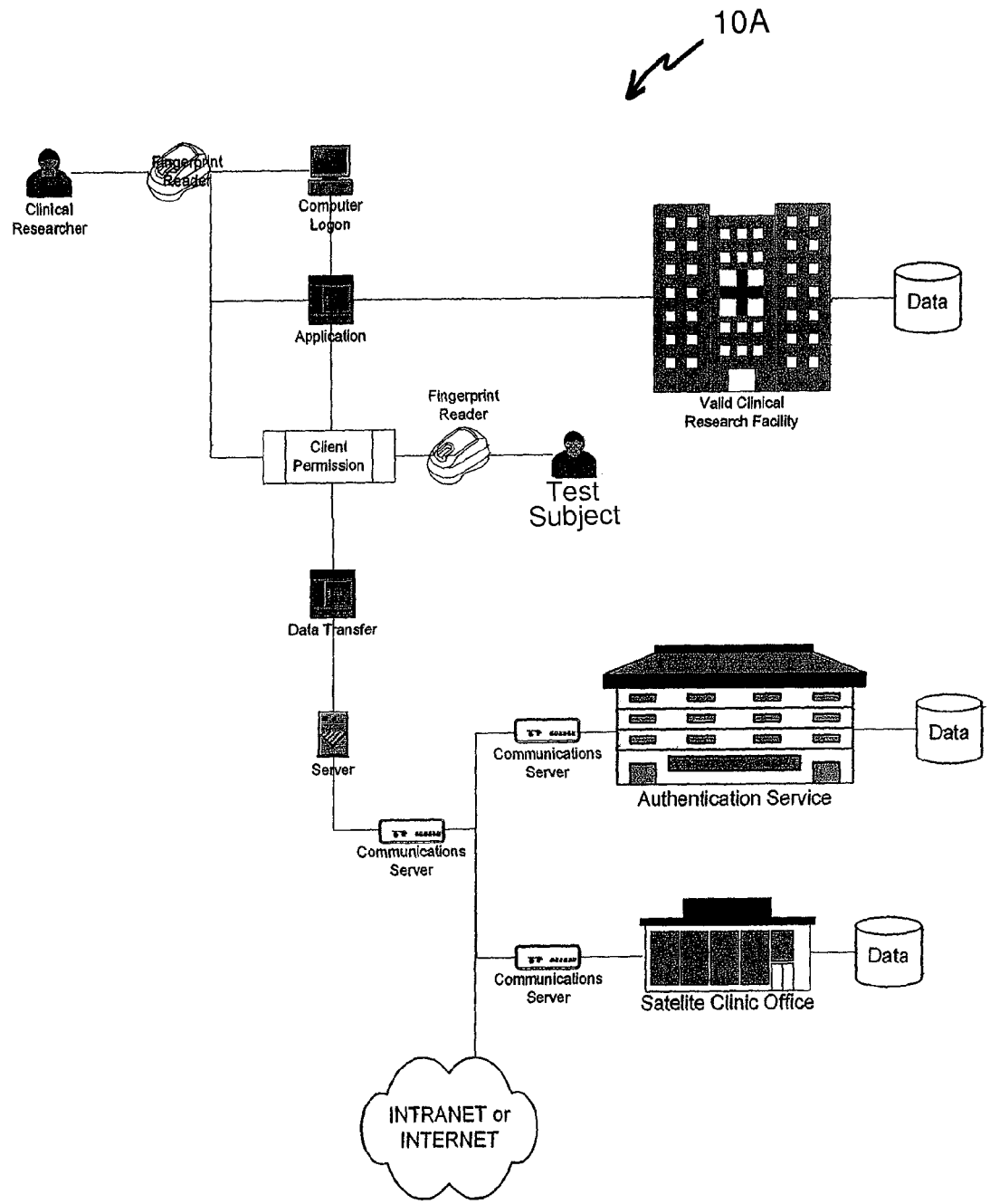
FIG. 2 depicts a point-of-use terminal which is spread over a large geographic area.

Having provided a general overview of the invention, an overview of a system and method are provided. In FIG. 1 there are shown two point-of-use terminals 10A, 10B, each communicating with a central database facility 13 via a communication channel 16. A point-of-use terminal 10 may be operated and maintained by a clinical research organization ("CRO"). Each point-of-use terminal 10A, 10B is shown having an admission workstation 19, a clinic workstation 22 and other workstations 25. The admission workstation 19 may be used to receive detailed information about a test-subject. The clinic workstation 22 may be used to authenticate the identity of a test-subject prior to administering a medication to the test-subject. The clinic workstation 22 may be thought of as a check-in facility. Both the admission workstation 19 and the clinic workstation 22 are shown having a biometric reader 28. In this case, the biometric reader 28 is a fingerprint scanner.

The CRO may maintain a local database 31 of information. The local database 21 may store information related to a clinical research effort, including the identities of the test-subjects that participated.

A method according to the invention may begin by executing a recruiting phase in which a clinical research organization recruits a test-subject and enrolls the test-subject. During the enrollment phase, the test-subject submits biometric samples, for example, fingerprints, facial images, iris scans, and/or other biometrics, for example via the admissions workstation 19. The submitted biometric samples may be, but are not required to be submitted with a personal identification number or code ("PIN"). This PIN may take the form of a standard non-unique four digit PIN number. For example, the PIN may be a birthday, address, social security number.

Information describing the submitted biometric sample(s) may be sent via the communication channel 16 and stored in a database of biometric sample information ("DBSI") 34. The biometric sample also may be compared using the local database 31 to determine if the prospective test-subject has previously worked with that CRO. If information corresponding to the test-subject is determined to be in the CRO's local database 31, a determination may be made as to whether the test-subject is suitable for the test. Such a determination may be made based on the test-subject's health history and previous CRO studies that the test-subject may have been associated with.

Figure 4:
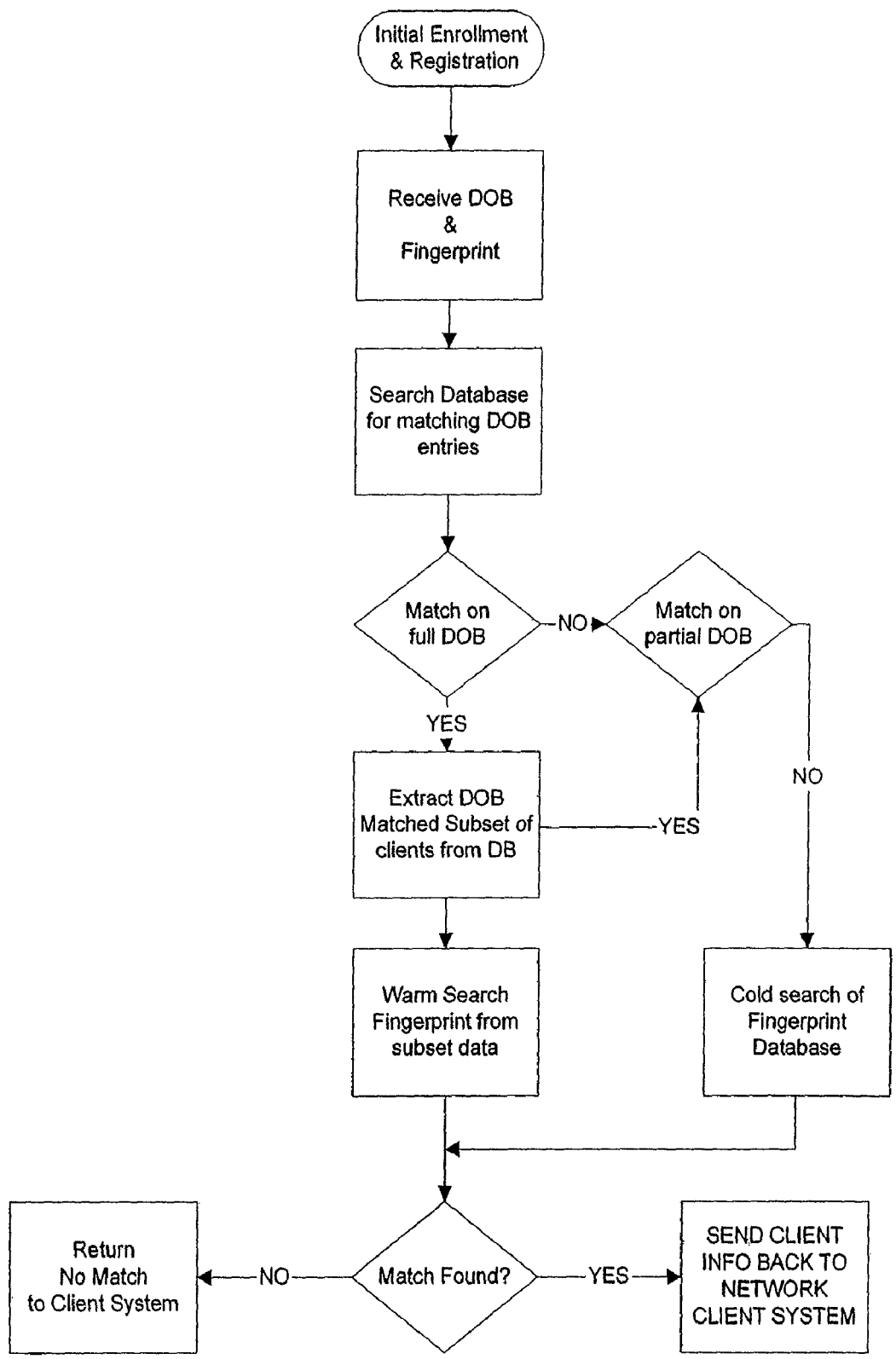
FIG. 4 is a flow diagram of an embodiment of the clinical research server application according to the invention.
Figure 5:
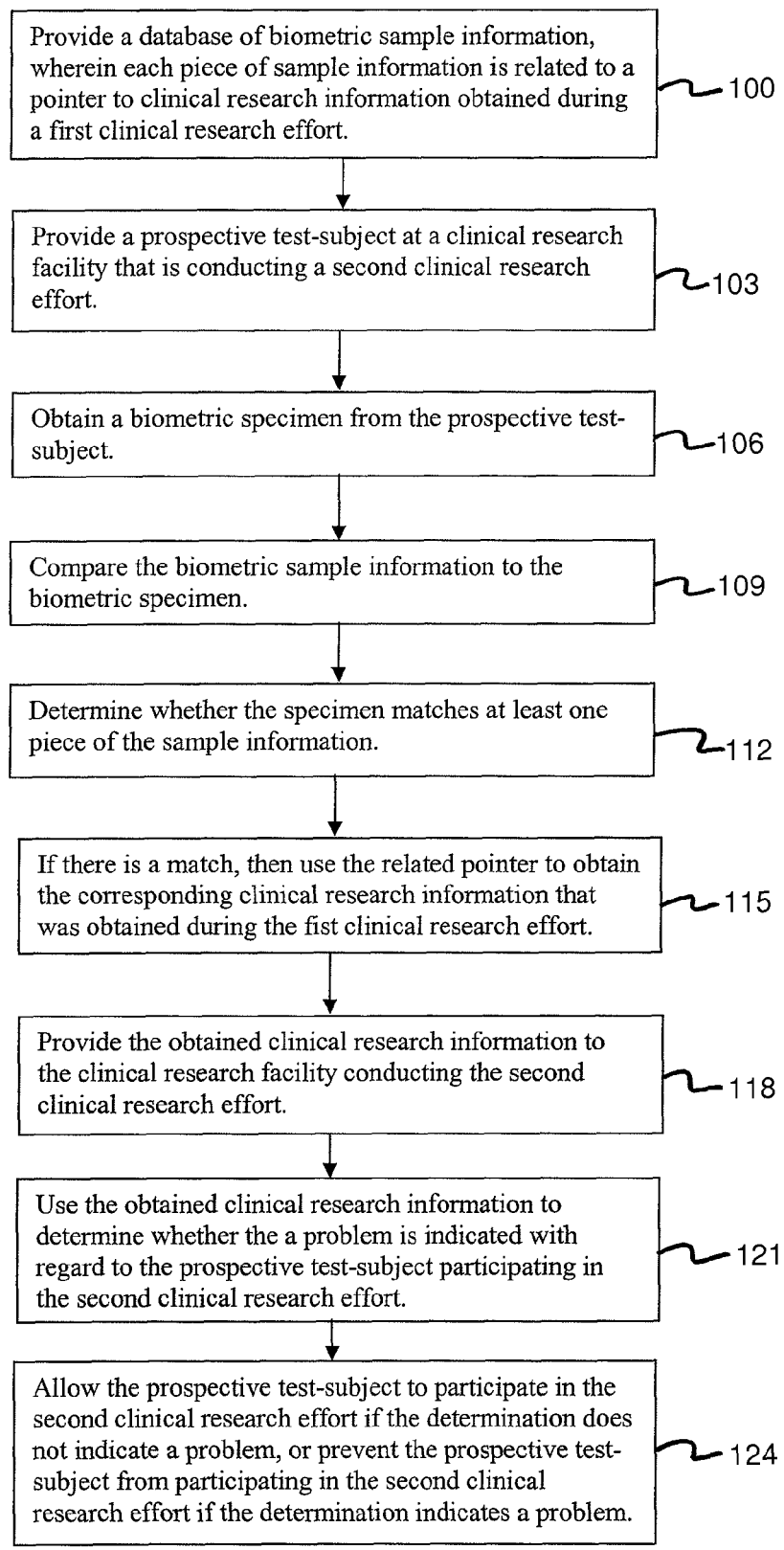
FIG. 5 is a flow diagram of a method according to the invention.

The test-subject's records and biometric sample(s) may also be compared with the records of other CROs or healthcare organizations to verify information that may be of value to the clinical research study. For example, information stored by one of the point-of-use terminals 10A in its local database 31 may be provided to the CRO that operates the other point-of-use terminal 10B. Using the information from the local database 31 of the point-of-use terminal 10A, the CRO that operates the other point-of-use terminal 10B may decide whether a particular test-subject is suitable for its clinical research effort. Once a test-subject has met the qualifications for a particular clinical research study, and has been verified as not participating in study hopping, the test-subject may be accepted for a particular clinical research study, and the clinical research study may be administered to the test-subject. FIG. 4 outlines the enrollment phase.

In the administration phase, the CRO may rely on a test-subject participating in the study in a conscientious and consistent manner. To this end, verification may be important. For example, each time a test-subject receives a pharmaceutical dose or medical procedure, the test-subject's identity may be verified via the clinic workstation 22 to insure the avoidance of false dispensing—a practice whereby a particular test-subject is required to take a dose of medication, but the test-subject has engaged an imposter to take the study dose of medication or receive the medical procedure for him. The invention may prevent false dispensing by having the test-subject submit one or more biometric specimens prior to receiving the prescribed dose or medical procedure. This verification and authentication process may insure that the proper doses are administered and the results recorded. At the same time it may allow for verification that a test-subject has not, in the meantime, engaged in study hopping by being recruited into another clinical research effort at the same facility or another independent facility.

As part of a system according to the invention, there may be subsystems designed to print bar codes and issue wrist bands specific to the test-subject upon biometric authentication and verification. This insures that study specimens are properly tagged and associated with the proper test-subject and that any supplies and apparatus required for the study are issued to the correct test-subject.

Biometric authentication may be carried out by the prospective test-subject providing one or more biometric specimens at a clinic work station 22 via one or more approved biometric readers 28. For example, the biometric reader 28 may be a fingerprint reader, hand geometry reader, facial recognition scanner, iris scanner, or a vascular scanner. A system according to the invention may use multiple biometrics to authenticate the identity of a test subject. A search and matching procedure may be carried out in order to determine whether the biometric specimen matches any of the samples in the DBSI 34. A "cold" search of the DBSI 34 may be made in which the specimens are compared to each sample in the DBSI 34 until a match is determined. This may require the comparison of a large number of samples.

In order to save time, the process of comparing specimens to samples may be limited to those samples that are related to a PIN. The PIN need not be unique, and may serve the function of search binning—that is, the PIN may allow a search and comparison procedure for the biometrics to take place on a subset of the information database, namely those biometric samples related to the PIN, so that the number of samples to be compared to the specimen is reduced and a result may be obtained faster. This procedure is also known as "warm" searching.

Once a match is determined between the specimen and a sample, the results may be given back to the CRO's point-of-use system 10 so that the CRO may proceed to the next required study procedure. An unsuccessful match may be reported back to the CRO so that the CRO and test-subject can resolve the reason for the result.

Having provided a general overview, and then an overview, details of embodiments of the invention are provided below. The invention may be embodied as a system for authorizing and authenticating transactions within a clinical research records database system. Portions of such a system, for example a particular point-of-use terminal 10A, may communicate with other similar portions (e.g. point-of-use terminal 10B) in an extended network or internet. The use of man-made personalized tokens need not be required in order to execute a transaction, an authorization and an authentication with a test-subject. A test-subject may be identified and flagged if enrolled more than once within the systems that are part of the network. A computer system or computer network system may be used to accomplish these goals.

In one system according to the invention, an operator accesses the CRO's point-of-use terminal 10 and logs on in order to activate a clinical research records database software program. A biometric sample and/or PIN, supplied by the operator, may be used to both grant access to the system and verify that the operator is authorized to use the system. At this point, the CRO can enter, modify, delete or update the records that may be made available as a result of successfully satisfying the authorization process. With the test-subject at hand, the operator may query the test-subject for certain information, for example, date of birth (DOB) or the test-subject's name, and may ask the test-subject for a biometric specimen. A biometric specimen may be a fingerprint, but the invention is not limited to fingerprints.

The system may be provided with the test-subject's DOB, used as a PIN, to avoid the requirement of a cold search of the DBSI 34, and may pass the test-subject's biometric specimen to the CRO's lookup engine. The CRO's lookup engine may determine that the test-subject does not have a record in the CRO's system. In response, the CRO may search the CRO's system using non-biometric information. If not enrolled in the CRO's system, the CRO may store the biometric provided by the possible test-subject, associate a unique number with the possible test-subject, and begin an enrollment process in which information about the possible test-subject is gathered and entered in the CRO's system.

To enroll a clinical research test-subject in the biometrics information database system, the following process may be used. The test-subject may enter his DOB, and a search may be made of the CRO database for existing records of the same DOB. If there is no match of the information, then additional searches may be conducted using the elements of the DOB, for example, the test-subject's last name in combination with only the year in the DOB may be used in an attempt to locate a record for the test-subject.

During enrollment, one or all of the test-subject's fingerprints may be enrolled, but to speed later database searches, the fingerprints of two index fingers may be enrolled. By enrolling more than one biometric, the number of instances in which an enrolled test-subject is not identified may be reduced. To minimize the number of instances in which a non-enrolled person is falsely identified as being enrolled, the system may maintain a complete audit log of all authorization attempts and their outcomes, no matter how trivial. A non-unique PIN may be used to minimize search times and a unique PIN may be used to prevent false acceptance. The PIN may be simply the user's name.

If a match is found, the CRO may receive a selectable list of possible candidate matches. Then the CRO may select the appropriate entry from the list and a CRO identification number may be assigned. If no matches are found, then a new test-subject identification number may be assigned, prior to proceeding to create a new record for the possible test-subject in the DBSI 34. Along with biometric sample information, certain demographics may be correlated with the biometric information in order to allow for easier searching in the future. Such demographics may include the possible test-subject's full name, an image of the possible test-subject, a driver's license number or social security number.

If the CRO determines that the test-subject has a record in the CRO's system, or once information about the possible test-subject is entered into the CRO's system, the CRO may associate the biometric sample with a unique identification number to be used in the clinical research effort. Then, when it is time to use the test-subject in a clinical research effort, a check-in facility of the CRO may be used by a prospective test-subject to provide a biometric specimen. Using the biometric specimen, a search is then made of the CRO database for existing records.

The CRO may then verify the identify of the prospective test-subject using local information in the CRO's local database. Once verified, the CRO may query the DBSI 34 as part of an effort to determine whether the prospective test-subject is enrolled in any other clinical research efforts.

Each CRO that is authorized to access and use the DBSI 34 will have a point-of-use terminal 10, which may include one or more computer workstations, at least one of which has a check-in facility, that may include a biometric reader 28, a network client software program (clinical research records management system) running on the computer workstation, and a clinical research database program for managing the local records of the CRO. A document scanner may also be included, in case the CRO desires to scan documents, such as driver's licenses or social security cards as part of an enrollment or check-in procedure. A communication server may also be included in order to facilitate communications via a communication channel between the CRO's computer workstation and the DBSI 34.

Such a point-of-use terminal 10 may allow a CRO to enter data into a pre-existing clinical records system or medical records database program and receive feedback allowing the discovery of multiple test-subject records and test-subject records for different test-subjects within the same test-subject record.

A system according to the invention may include a network client shell, which may be a computer software program residing on the point-of-use terminal. The network client shell may operate in conjunction with a pre-existing clinical research records database software system, and may intercept keystrokes and actions of the terminal, determine applicability, and if needed query for biometric input and transmit the collected inputs to a microprocessor that serves as an interface between the CRO's point-of-use terminal 10 and the DBSI 34. The network client shell may receive responses back from the DBSI 34 and pass them to the CRO's local records system after using them in conjunction with the operator and/or test-subject to verify the data and/or permissions authorized.

A system according to the invention may also include software for handling information queries received from the network client applications, verifying identities biometrically and retrieving and transmitting data items needed by the network client system that it supports. It may be hosted remotely over a network or the internet or may reside on the same system that the network client utilizes.

A check-in facility is referenced above, and that reference notes that a biometric reader 28 may be used. Such a biometric reader 28 may be used by a possible test-subject and/or a prospective test-subject to provide a biometric sample or specimen, respectively. The biometric reader 28 may be a device that gathers biometric information for use in authorizing electronic biometric transactions. Each biometric reader 28 may conduct one or more of the following operations:

gather biometric samples and/or specimens from test-subjects;

optionally receive a PIN from a test-subject;

provide secure communication between the biometric reader 28 and the clinical research records;

process information provided to the biometric reader 28 in order to encrypt the information;

provide secure storage of secret encryption keys;

optionally store and retrieve a unique identification code for authenticating the biometric reader 28 to other hardware in the system or network;

have an enclosure to protect components from unauthorized tampering;

have a monitor for displaying information to allow users to approve or cancel an action;

store, verify, and retrieve an authenticator digital identification code or certificate.

Biometric samples and specimens may be gathered using a biometric sensor located within the biometric reader 28. The biometric sensor may be a finger print reader, however, it is understood that other types of biometric sensors such as a hand geometry reader, an iris scanner, a retinal scanner, a vascular pattern recognizer, a facial recognition system, or more than one of these types of sensors may be included in the biometric reader 28. To simplify this description of the invention, a biometric reader 28 having only a single finger print reader will be discussed. But it will be recognized that other configurations are possible.

Optionally the biometric reader 28 may have a biometric fraud detection system that will assure that biometric information gathered by the biometric reader 28 is provided by a real person, instead of by a copy or replica of the biometric. One manner of accomplishing this is to include a temperature sensor with the biometric reader 28 in order to assure that the biometric sample or specimen is provided by an object having a temperature within the range expected for a human being.

For systems employing a PIN, the biometric reader 28 may include a keypad which allows a test-subject to press keys associated with the PIN.

Communication security between the various components of the point-of-use terminal, or between a point-of-use terminal and the DBSI 34 may be provided by encrypting information that is transmitted. Many methods of encrypting information are well known, and will not be discussed herein in detail. For example, an encryption system using public/private keys may be used to encrypt information that passes between system components.

Each biometric reader 28 may have a hardware identification code that may be registered with a data processing center at the time the biometric reader 28 is manufactured or placed into service. By using a hardware identification code, the biometric reader 28 may be uniquely identifiable to the data processing center in all transmissions from that device. This hardware identification code may be permanently stored in write-once memory.

The biometric reader's 28 physical security may be assured by the use of tamper-detect circuitry, an enclosure that cannot be easily opened without visibly damaging the enclosure, erasable memory for critical secrets such as encryption keys, write-once memory for hardware identification, tight integration of all components, and "potting" of exposed circuitry.

Optionally, the biometric reader 28 may validate public key digital certificates. In one embodiment, public keys of a particular certifying authority may be initially stored in the biometric reader 28 at the time of manufacture. This provides a mechanism to verify an authenticator's digital certificates that are signed by the certifying authority or agency.

The point-of-use terminal may include software designed to manage the activities of the point-of-use terminal. Such software may allow a microprocessor of the terminal to allow acceptance of a biometric sample or biometric specimen provided to the biometric reader 28, and provide the sample or specimen to another computer.

Having described the system it will be recognized that a method according to the invention may be executed as follows. A database may be provided 100. The database may have stored therein biometric sample information. Each piece of sample information may have been received from a test-subject in a first clinical research effort, and each piece of sample information may be related to a pointer to clinical research information obtained during the first clinical research effort. The pointer may point to a database other than the database that has the biometric sample information.

A prospective test-subject may be provided 103 at a clinical research facility conducting a second clinical research effort. A biometric specimen may be obtained 106 from the prospective test-subject, and compared 109 to the biometric sample information. A determination 112 may be made as to whether the specimen matches at least one piece of the sample information. If the specimen matches at least one piece of sample information, then the related pointer may be used 115 to obtain the corresponding clinical research information that was obtained during the first clinical research effort. The obtained clinical research information may be provided 118 to the clinical research facility conducting the second clinical research effort, and used to determine 121 whether the obtained clinical research information indicates a problem with the prospective test-subject participating in the second clinical research effort. Depending on the outcome of the determination, certain actions may be taken 124. For example, the prospective test-subject may be allowed to participate in the second clinical research effort if the determination does not indicate a problem. Or the prospective test-subject may be prevented from participating in the second clinical research effort if the determination indicates a problem.

U.S. provisional patent application No. 60/739,607 discloses additional details about the invention and additional embodiments of the invention. The disclosure of that patent application is incorporated by this reference.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A clinical research management system, comprising:
   a database of biometric sample information, at least some of the pieces of sample information having been received from a test-subject in a first clinical research effort, and each piece of sample information having a related pointer to a location of clinical research information obtained during the first clinical research effort;
   a check-in facility at a clinical research facility that is conducting a second clinical research effort, the check-in facility having a biometric reader;
   a communication channel;
   a microprocessor, programmed to: (a) receive from the communication channel, information corresponding to a biometric specimen received at the check-in facility, (b) compare the biometric specimen to the biometric sample information (c) determine whether the specimen matches at least one piece of the sample information in the database to identify a matching piece of sample information, (d) identify the pointer in the database that is related to the matching piece of sample information, (e) use the identified pointer to obtain the corresponding clinical research information that was obtained during the first clinical research effort, (f) provide the obtained corresponding clinical research information to the clinical research facility conducting the second clinical research effort.

2. The management system of claim 1, further comprising a second database, the second database having stored therein the clinical research information obtained from the test subject during the first clinical research effort.

3. A clinical research management network, comprising:
   a first database of biometric sample information, at least some of the pieces of sample information having been received from a test-subject in a first clinical research effort, and each of those pieces of sample information having a related pointer to a location of clinical research information obtained during the first clinical research effort;
   a plurality of check-in facilities, each check-in facility being located at a clinical research facility that is conducting clinical research that is not related to the first clinical research effort, and each check-in facility has a biometric reader;
   a microprocessor in communication with the check-in-facilities and the first database, and programmed to: (a) receive a biometric specimen received at the biometric reader of one of the check-in facilities, (b) compare the biometric specimen to the biometric sample information (c) determine whether the specimen matches at least one piece of the sample information in the database to identify a matching piece of sample information, (d) identify the pointer in the database that is related to the matching piece of sample information, (e) use the identified pointer to obtain the corresponding clinical research information that was obtained during the first clinical research effort, (f) provide the obtained corresponding clinical research information to at least one of the clinical research facilities conducting clinical research that is not related to the first clinical research effort.

4. The management network of claim 3, further comprising a plurality of second databases, each of the second databases having stored therein clinical research information pointed to by the pointers of the first database, and wherein at least one of the second databases has the clinical research information obtained during the first clinical research effort.

5. A method of managing clinical research, comprising:
   providing a database having biometric sample information, each piece of sample information having been received from a test-subject in a first clinical research effort, and each piece of sample information having a related pointer to a location of clinical research information during the first clinical research effort;
   providing a prospective test-subject at a clinical research facility conducting a second clinical research effort;
   obtaining a biometric specimen from the prospective test-subject;
   comparing the biometric specimen to the biometric sample information;
   determining whether the specimen matches at least one piece of the sample information in the database;
   if the specimen matches at least one piece of sample information, then using the related pointer to obtain the corresponding clinical research information that was obtained during the first clinical research effort;
   providing the obtained clinical research information to the clinical research facility conducting the second clinical research effort;
   determining whether the obtained clinical research information indicates a problem with the prospective test-subject participating in the second clinical research effort, to provide a determination;
   acting on the determination by allowing the prospective test-subject to participate in the second clinical research effort if the determination does not indicate a problem, or preventing the prospective test-subject from participating in the second clinical research effort if the determination indicates a problem.

6. The method of claim 5, wherein the pointer points to a database other than the database having biometric sample information.

* * * * *